(12) United States Patent
Tian et al.

(10) Patent No.: US 11,549,133 B2
(45) Date of Patent: Jan. 10, 2023

(54) PREPARATION METHOD OF AMYLODEXTRIN

(71) Applicant: Jiangnan University, Wuxi (CN)

(72) Inventors: Yaoqi Tian, Wuxi (CN); Xintian Wang, Wuxi (CN); Rongrong Ma, Wuxi (CN); Jinling Zhan, Wuxi (CN)

(73) Assignee: Jiangnan University, Wuxi (CN)

( * ) Notice: Subject to any disclaimer, the term of this patent is extended or adjusted under 35 U.S.C. 154(b) by 230 days.

(21) Appl. No.: 17/094,962

(22) Filed: Nov. 11, 2020

(65) Prior Publication Data

US 2021/0062236 A1 Mar. 4, 2021

Related U.S. Application Data

(63) Continuation of application No. PCT/CN2020/074489, filed on Feb. 7, 2020.

(30) Foreign Application Priority Data

Jan. 17, 2020 (CN) .......................... 202010051998.3

(51) Int. Cl.
| | | |
|---|---|---|
| *C12P 19/16* | (2006.01) | |
| *C08B 30/18* | (2006.01) | |
| *C12P 19/04* | (2006.01) | |
| *C12P 19/14* | (2006.01) | |
| *B01J 19/10* | (2006.01) | |

(52) U.S. Cl.
CPC ............... *C12P 19/16* (2013.01); *B01J 19/10* (2013.01); *C08B 30/18* (2013.01); *C12P 19/04* (2013.01); *C12P 19/14* (2013.01)

(58) Field of Classification Search
CPC .......... C08B 30/18; C12P 19/14; C12P 19/16; B01J 19/10
See application file for complete search history.

(56) References Cited

U.S. PATENT DOCUMENTS

2011/0053888 A1* 3/2011 Gil Hernandez ......... A61P 3/02
426/2

FOREIGN PATENT DOCUMENTS

| CN | 101495642 A | | 7/2009 | |
|---|---|---|---|---|
| CN | 106906266 | * | 4/2017 | .............. C12P 19/14 |
| CN | 109295129 | * | 2/2019 | .............. C12P 19/00 |
| WO | 02097077 A1 | | 12/2002 | |

OTHER PUBLICATIONS

English machine translation of CN 106906266, from worldwide.espacenet.com (Year: 2017).*
English machine translation of CN 109295129, from worldwide.espacenet.com (Year: 2019).*
Sun jun-liang, et al.,Ultrasound-assisted Enzymatic Hydrolysis of Corn Starch for Preparing Dextrin, Food Science, 126 2009, vol. 30, No. 18.

* cited by examiner

*Primary Examiner* — Eric Olson
(74) *Attorney, Agent, or Firm* — IPRO, PLLC; Na Xu

(57) ABSTRACT

The disclosure relates to a preparation method of a amylodextrin and belongs to the technical field of starch chemical modification. According to the method, de-clustering and complexation effects of ultrasonic waves are used to achieve de-clustering of a starch chain and complexation of an amorphous region and an emulsifier, and then α-amylase and pullulanase are used to achieve complex enzymolysis. Because the amorphous region and the emulsifier form a complex which is resistant to enzymolysis, the amorphous region is prevented from being destroyed. Finally, dextrins of different molecular weights are separated by a membrane separation method, so as to obtain a amylodextrin product with low polydispersity coefficient and narrow molecular weight distribution, and the starch comprehensive utilization efficiency is increased to 70% or above.

10 Claims, No Drawings

PREPARATION METHOD OF AMYLODEXTRIN

TECHNICAL FIELD

The disclosure relates to a preparation method of amylodextrin and belongs to the technical field of starch chemical modification.

BACKGROUND

The molecular weight and distribution of amylodextrin are closely related to properties and applications thereof. At present, amylodextrin are mainly prepared by using amylose as a substrate for hydrolysis, amylopectin as a substrate for enzymatic debranching and glucose as a substrate for enzymatic polymerization. The amylodextrin prepared by these three methods all have the problem of wide molecular weight distribution, which limits the application range. Therefore, restricting starch degradation, obtaining new amylodextrin products with uniform degree of polymerization by classification and broadening application in chemical engineering, medicine, food and other fields are important ways for starch and other agricultural and sideline products to add value.

Starch is comprised of about 40% crystalline region (homogeneous dextrin unit) and about 60% amorphous region (homogeneous dextrin unit). Usually, an enzymolysis method is used to hydrolyze the amorphous region to obtain a uniform dextrin product in the crystalline region, but the starch utilization rate is as low as 30%. In the disclosure, the amorphous region of the starch is protected by complexing with an emulsifier, then the preparation of amylodextrin products with different degrees of uniformity is realized by a complex enzymolysis technology, and the utilization rate of the starch is greatly increased to 70%.

The complexation methods of starch and an emulsifier include an alkali-alcohol method and a drying method. The complexation rate can reach 30%-65%, which mainly depends on the starch clustering structure and the emulsifier type. However, these methods produce waste acid and waste alkali, leading to production of a large amount of inorganic waste water during industrial production. In the disclosure, ultrasonic de-clustering, ultrasonic induced emulsifier complexation and other technologies are adopted to make the starch amorphous region-emulsifier complexation rate up to 65% in a single water reaction system.

Dextrin classification methods mainly include membrane technology classification and phase transition classification. Phase transition classification is mainly to adjust the concentration of ethanol to sequentially precipitate polymers with different molecular weights. The process requires a large amount of ethanol that is high in cost, causes high environmental pollution and is not suitable for industrial large-scale dextrin classification. The disclosure adopts a membrane separation method, which can realize classified preparation of new dextrin products with uniform molecular weight on a large scale.

SUMMARY

The objective of the disclosure is to solve the problems of low yield and wide molecular weight distribution of a dextrin obtained by enzymolysis of starch, the yield of a dextrin is increased by complexing with an emulsifier to protect the amorphous region, and a amylodextrin component with uniform polymerization degree is obtained through a membrane separation technology.

The disclosure discloses a preparation method of amylodextrin. The method adopts ultrasonic waves to directly de-cluster starch without thermal gelatinization; then an emulsifier is added for ultrasonic complexation, enzymolysis and membrane separation to obtain amylodextrin. The method is to use de-clustering and complexation effects of ultrasonic waves to achieve de-clustering of a starch chain and complexation of the amorphous region and the emulsifier, and then use α-amylase and pullulanase to achieve complex enzymolysis. Because the amorphous region and the emulsifier form a complex which is resistant to enzymolysis, the amorphous region is prevented from being destroyed. Finally, dextrins of different molecular weights are separated by a membrane separation method, so as to obtain an amylodextrin product with low polydispersity coefficient and narrow molecular weight distribution.

In an embodiment of the disclosure, the method includes the following steps:

(1) ultrasonic de-clustering: adding water into waxy corn starch for blending and ultrasonic treatment;

(2) ultrasonic complexation: adding an emulsifier into a raw material obtained in step (1) for ultrasonic treatment;

(3) complex enzymolysis: adding a buffer into a product obtained in step (2) for blending, and adding α-amylase and pullulanase for complex enzymolysis;

(4) ethanol extraction: adding an enzymolysis product obtained in step (3) into absolute ethanol to dissolve emulsifier;

(5) membrane separation: performing membrane separation on a product obtained in step (4) to obtain a dextrin; and (6) drying: spray drying a product obtained after membrane separation in step (5) to obtain a finished product.

In an embodiment of the disclosure, in step (1), water is added into the starch to prepare 5%-10% starch slurry, the ultrasonic working frequency is 20-30 kHz, the treatment power is 500-600 W, the temperature is 20-25° C., and the action time is 5-15 minutes.

In an embodiment of the disclosure, in step (2), the added emulsifier is glycerol monostearate or palmitic acid, the addition amount is 3%-5% mass of the starch, the ultrasonic working frequency is 20-30 kHz, the treatment power is 500-600 W, the temperature is 40-50° C., and the action time is 20-30 minutes.

In an embodiment of the disclosure, in step (3), the pH of a product obtained in step (2) is adjusted to 6.0-6.5 with a phosphate buffer.

In an embodiment of the disclosure, an emulsion in step (3) is heated to 50-60° C. in a water bath, medium-temperature α-amylase and pullulanase are added, the addition amount of pullulanase is 30-40 ASPU/g dry starch, the addition amount of α-amylase is 20-30 ASPU/g dry starch, enzymolysis is carried out for 3-4 hours, then the mixture is put into a boiling water bath for 5-10 minutes to inactivate medium-temperature α-amylase and pullulanase so as to terminate a reaction, and centrifugation is carried out to obtain a supernatant.

In an embodiment of the disclosure, in step (4), the amount of absolute ethanol is 1-1.2 times the volume of the starch-emulsifier complex solution.

In an embodiment of the disclosure, in step (5), ultrafiltration membranes used for membrane separation are hollow fiber membranes with molecular weight cutoffs of 5000 Da and 2000 Da for membrane classification.

In an embodiment of the disclosure, in step (6), the inlet air temperature during spray drying is 140-160° C.

The disclosure discloses amylodextrin prepared by the above method.

In an embodiment of the disclosure, the content of DP10-30 in the amylodextrin is higher than 70%.

The disclosure discloses application of the amylodextrin in preparation of a microcapsule as an embedding material for main components of macromolecular cod liver oil such as DHA and EPA.

The Beneficial Effects of the Disclosure:

(1) The disclosure uses ultrasonic de-clustering to avoid the situation that the starch crystallization region is degraded into small molecular sugars and other fragments by subsequent enzymolysis, the amorphous region of the starch is protected in combination with complexation of an emulsifier, and then the amylodextrin products with different degrees of uniformity is prepared by adopting a complex enzymolysis technology. The starch comprehensive utilization efficiency is increased by 70% or above. In addition, the increase effect of the starch utilization rate after combined treatment of ultrasonic de-clustering and ultrasonic complexation is better than the total effect of separate ultrasonic de-clustering and separate ultrasonic complexation, indicating that ultrasonic de-clustering and ultrasonic complexation support each other in increasing the starch utilization rate and has a synergistic effect during combined treatment.

(2) In the disclosure, an ultrasonic induced emulsifier complexation technology is adopted to make the starch-emulsifier complexation rate of the starch amorphous region greatly improved to 65%.

(3) The content of DP10-30 in the amylodextrin prepared by the production process of the disclosure can reach about 80%, the yield is high, the molecular weight distribution is even, the production cost is low, continuous industrial production is easy, the use of acid and alkali reagents is reduced, and there is little environmental pollution.

DETAILED DESCRIPTION

The preferred embodiments of the disclosure will be described below. It should be understood that the embodiments are for better explaining the disclosure and are not intended to limit the disclosure.

1. The Starch Utilization Rate

Namely, the yield of amylodextrin is expressed by the ratio of the total mass of all dextrin components after membrane separation to the mass of waxy corn starch used. A calculation formula is as follows:

Starch utilization rate $$(\%) = \frac{\text{Total mass of linear-chain dextrin after membrane separation (mg)}}{\text{Mass of waxy corn starch (mg)}} * 100\%$$

2. Measurement of the Waxy Corn Starch-Emulsifier Complexation Rate

The complexation rate is expressed by the utilization ratio of a complex to an emulsifier. The content of the emulsifier in the complex is expressed by the amount of the emulsifier washed off in step (4) after the residual emulsifier is washed off in step (2), and the complexation rate is calculated according to the following formula:

Waxy Corn Starch-Emulsifier Complexation Rate $$(\%) = \frac{\text{Emulsifier content of complex (mg)}}{\text{Addition amount of emulsifier (mg)}} * 100\%$$

3. Chain Length Distribution of Amylodextrin

The chain length distribution of amylodextrin is detected by high performance anion exchange chromatography (HPAEC-PAD) equipped with a pulse current detector. The HPAEC-PAD chromatography system is equipped with an ED40 pulsed amperometric detector. The chromatography column model is Dionex CarboPAC PA200 (250*4 mM I.D.). The eluent A is a 100 mmol/L NaOH solution, and the eluent B is a 100 mmol/L NaOH solution containing 600 mmol/L sodium acetate. Linear gradient elution is adopted: a 20% eluent B is used at 0 minute, and a 100% eluent B is used at 60 minutes. The flow rate is 1 ml/min, and the injection volume is 25 μl.

α-amylase and pullulanase are purchased from Sigma.

EXAMPLE 1

(1) Ultrasonic de-clustering: 5%-10% waxy corn starch slurry is prepared and stirred evenly for ultrasonic treatment, the ultrasonic working frequency is 25 kHz, the treatment power is 600 W, the temperature is 25° C., the action time is 3 seconds at an interval of 5 seconds, and the total treatment time is 10 minutes.

(2) Ultrasonic complexation: glyceryl monostearate which is 5% mass of the waxy corn starch is added into the starch slurry after ultrasonic treatment and stirred evenly, the ultrasonic working frequency is 20 kHz, the treatment power is 500 W, the temperature is 40° C., the action time is 3 seconds at an interval of 5 seconds, and the total ultrasonic treatment time is 20 minutes.

(3) Complex enzymolysis: the pH of a starch-glyceryl monostearate complex solution is adjusted to 6.0 with a phosphate buffer, the solution is heated to 50° C. in a water bath, medium-temperature α-amylase and pullulanase are added, the addition amount of pullulanase is 30 ASPU/g dry starch, the addition amount of α-amylase is 30 ASPU/g dry starch, the mixture is hydrolyzed in a water bath at 50° C. for 3-4 hours, the mixture is put into a boiling water bath for 5 minutes to inactivate medium-temperature α-amylase and pullulanase so as to terminate a reaction, and centrifugation is carried out to obtain a supernatant.

(4) Ethanol extraction: an enzymolysis product is added into absolute ethanol to dissolve glyceryl monostearate.

(5) Membrane separation: hollow fiber membranes with molecular weight cutoffs of 5000 Da and 2000 Da are used for membrane separation under the conditions that the membrane effective region is 0.4 m$^2$, the operation temperature is 40° C. and the operation pressure is 15 kPa.

(6) Drying: a component obtained after membrane separation is spray dried to obtain a finished amylodextrin product.

EXAMPLE 2

(1) Ultrasonic de-clustering: 5%-10% waxy corn starch slurry is prepared and stirred evenly for ultrasonic treatment, the ultrasonic working frequency is 25 kHz, the treatment power is 600 W, the temperature is 25° C., the action time is 3 seconds at an interval of 5 seconds, and the total treatment time is 10 minutes.

(2) Ultrasonic complexation: palmitic acid which is 3% mass of the waxy corn starch is added into the starch slurry after ultrasonic treatment and stirred evenly, the ultrasonic working frequency is 20 kHz, the treatment power is 500 W, the temperature is 40° C., the action time is 3 seconds at an interval of 5 seconds, and the total ultrasonic treatment time is 20 minutes.

(3) Complex enzymolysis: the pH of a starch-palmitic acid complex solution is adjusted to 6.0 with a phosphate buffer, the solution is heated to 50° C. in a water bath, medium-temperature α-amylase and pullulanase are added, the addition amount of pullulanase is 40 ASPU/g dry starch, the addition amount of α-amylase is 20 ASPU/g dry starch, the mixture is hydrolyzed in a water bath at 50° C. for 3-4 hours, the mixture is put into a boiling water bath for 5 minutes to inactivate medium-temperature α-amylase and pullulanase so as to terminate a reaction, and centrifugation is carried out to obtain a supernatant.

(4) Ethanol extraction: an enzymolysis product is added into absolute ethanol to dissolve palmitic acid.

(5) Membrane separation: hollow fiber membranes with molecular weight cutoffs of 5000 Da and 2000 Da are used for membrane separation under the conditions that the membrane effective region is 0.4 m$^2$, the operation temperature is 40° C. and the operation pressure is 15 kPa.

(6) Drying: a component obtained after membrane separation is spray dried to obtain a finished amylodextrin product.

COMPARATIVE EXAMPLE 1

Ultrasonic de-clustering (1) and ultrasonic complexation (2) in Example 1 are omitted, and other conditions or parameters are the same as those in Example 1. This example is equivalent to a blank control. The complexation rate and the starch utilization rate are extremely low, indicating that the waxy corn starch and the emulsifier can hardly form a complex without any external force, and subsequent enzymolysis is not facilitated.

COMPARATIVE EXAMPLE 2

Ultrasonic de-clustering (1) in Example 1 is omitted, and other conditions or parameters are the same as those in Example 1. Compared with Example 1, the complexation rate and the starch utilization rate are reduced to 32% and 37% respectively, because the starch chain is not fully stretched but is still in an aggregated state, which hinders complexation of the amorphous region and the emulsifier. Therefore, ultrasonic treatment in step (1) has the effect of de-clustering the starch chain.

COMPARATIVE EXAMPLE 3

Ultrasonic complexation (2) in Example 1 is omitted, and other conditions or parameters are the same as those in Example 1. Compared with Example 1, after an emulsifier is added, ultrasonic treatment is not used to promote complexation between the amorphous region and the emulsifier, and the final complexation rate and the starch utilization rate are as low as 36% and 41% respectively. Therefore, it can be explained that ultrasonic treatment in step (2) has the effect of promoting complexation between the amorphous region of the starch and the emulsifier.

COMPARATIVE EXAMPLE 4

Ultrasonic de-clustering (1) in Example 1 is changed into gelatinization: 5%-10% waxy corn starch slurry is prepared, put into a boiling water bath for 40 minutes, stirred while boiling and cooled to 60° C. for heat preservation. Compared with Example 1, the complexation rate and the starch utilization rate are reduced to 34% and 36% respectively.

TABLE 1

| Sample | Complexation rate/% | Starch utilization rate/% |
|---|---|---|
| Example 1 | 65 | 72 |
| Example 2 | 58 | 69 |
| Comparative Example 1 | 0.75 | 13 |
| Comparative Example 2 | 32 | 37 |
| Comparative Example 3 | 36 | 41 |
| Comparative Example 4 | 34 | 36 |

It can be seen from Table 1 that through ultrasonic de-clustering and ultrasonic induced emulsifier complexation (namely Example 1), the starch amorphous region-emulsifier complexation rate and the starch utilization rate in a water reaction system can reach up to 65% and 72% respectively. Comparative Example 1 is equivalent to a blank control. The waxy corn starch is directly enzymatically hydrolyzed after an emulsifier is added. Because the starch chain is not stretched, it is almost impossible to achieve complexation, and only the surface parts of starch granules can be enzymatically hydrolyzed. Without ultrasonic de-clustering or ultrasonic complexation (Comparative Example 2 and Comparative Example 3), the starch-emulsifier complex rates in the amorphous region are 32% and 36% separately, and the starch utilization rates are 37% and 41% respectively, which are increased by 24% and 28% respectively in comparison with those of the blank group. On the other hand, Comparative Examples 2 to 3 are compared with Example 1, the increase effect (increased by 59%) of the starch utilization rate after combined treatment of ultrasonic de-clustering and ultrasonic complexation is better than the total effect (24%+28%=52%) of separate ultrasonic de-clustering and separate ultrasonic complexation, indicating that ultrasonic de-clustering and ultrasonic complexation support each other in increasing the starch utilization rate and has a certain synergistic effect during combined treatment. Ultrasonic de-clustering (1) in Example 1 is replaced with gelatinization in Comparative Example 4, which is also the common method of preparing amylodextrin currently. In this step, the starch crystallization region is destroyed at a high temperature, the starch is decomposed into many small molecule sugars and other fragments (see Table 2 for details) in the enzymolysis process, and the total amylodextrin yield is greatly reduced; compared with Example 1, the complexation rate and the starch utilization rate are reduced to 34% and 36% respectively, indicating that ultrasonic de-clustering can protect the starch crystallization region when performed at a temperature lower than the starch gelatinization temperature, so as to avoid the situation that the starch crystallization region is degraded into small molecular sugars and other fragments in subsequent enzymolysis, thereby obtaining amylodextrin with uniform molecular weight distribution to increase the complexation rate and the starch utilization rate. It can be explained that through the combined effects of ultrasonic de-clustering and ultrasonic accelerated emulsifier complexation, not only is the destruction of the starch crystallization region avoided, but also the starch amorphous region-emulsifier complex rate and the starch utilization rate are increased.

TABLE 2

Chain length distribution of amylodextrin

| | Membrane molecular weight cutoff (Da) | DP < 10 (%) | DP10-30 (%) | DP > 30 (%) | Content (%) |
|---|---|---|---|---|---|
| Example 1 | <2000 | 86.7 ± 0.8 | 12.6 ± 0.4 | 0.7 ± 0.5 | 6.1 ± 0.1 |
| | 2000-5000 | 0.4 ± 0.3 | 92.4 ± 0.1 | 7.2 ± 0.7 | 81.9 ± 0.3 |
| | >5000 | 16.5 ± 0.4 | 15.6 ± 0.6 | 67.9 ± 0.2 | 12.0 ± 0.8 |
| Example 2 | <2000 | 84.8 ± 0.5 | 11.9 ± 0.2 | 3.3 ± 0.6 | 5.4 ± 0.4 |
| | 2000-5000 | 1.8 ± 0.1 | 91.7 ± 0.3 | 6.5 ± 0.7 | 78.7 ± 0.5 |
| | >5000 | 16.5 ± 0.6 | 13.2 ± 0.7 | 70.3 ± 0.1 | 15.9 ± 0.6 |
| Comparative Example 4 | <2000 | 91.5 ± 0.8 | 6.4 ± 0.6 | 2.1 ± 0.3 | 25.3 ± 0.1 |
| | 2000-5000 | 15.6 ± 0.4 | 80.4 ± 0.8 | 4.0 ± 0.5 | 69.8 ± 0.6 |
| | >5000 | 24.6 ± 0.7 | 16.9 ± 0.3 | 58.5 ± 0.3 | 4.9 ± 0.7 |

Note:
DP refers to degree of polymerization

It can be seen from Table 2 that the amylodextrin obtained by complex enzymolysis of the waxy corn starch is divided into three components through membrane separation in Examples 1 and 2, main ingredients of the component with a molecular weight of lower than 2000 Da include small molecular glucose, ethanol, an emulsifier and other substances, and the content is relatively low, only 5.4%-6.1%; the component with a molecular weight higher than 2000 Da is the amylodextrin with high purity, the content of the amylodextrin with the molecular weight cutoff of 2000-5000 Da, i.e., DP10-30 is the highest, accounting for 78.7%-81.9%; the content of the amylodextrin with the molecular weight cutoff higher than 5000 Da, i.e., DP>30 is the second, accounting for 12%-15.9%. It can be explained that the degree of polymerization of the amylodextrin obtained in the disclosure is mostly distributed between 10 and 30. In Comparative Example 4, the starch is gelatinized at a high temperature first. This step destroys the starch crystallization region, and starch molecules are degraded into many small molecule sugars and other fragments during complex enzymolysis. Therefore, the content of components with molecular weight lower than 2000 Da is higher than that in Example 1 and Example 2, accounting for about 25%.

What is claimed is:

1. A method of preparing amylodextrin, which comprises the following steps performed in the following order:
    (a) exposing a mixture of water and corn starch in a 5% to 10% starch slurry to ultrasonic waves,
    (b) adding an emulsifier to the starch slurry,
    (c) exposing the starch slurry of (b) to ultrasonic waves to obtain complexation,
    (d) incubating the complexation with added enzymes to produce a dextrin product, wherein the enzymes comprise at least α-amylase and pullalanase, and
    (e) separating dextrins of differing molecular weights by membrane separation, thereby obtaining the amylodextrin.

2. The method according to claim 1, wherein the method further comprises:
    between steps (d) and (e), extracting the dextrin product by adding the dextrin product obtained in step (d) to absolute ethanol; and
    spray drying the amylodextrin obtained in step (e).

3. The method according to claim 1, wherein in step (a), the ultrasonic treatment is performed at an ultrasonic treatment power of 500 W to 600 W, for 5 minutes to 15 minutes.

4. The method according to claim 1, wherein the emulsifier is glyceryl monostearate or palmitic acid, and wherein the emulsifier is added to a final concentration of 3% to 5% mass of the starch.

5. The method according to claim 1, wherein in step (b), the ultrasonic treatment is performed at an ultrasonic treatment power of 500 W to 600 W, a temperature of 40° C. to 50° C., for 20 minutes to 30 minutes.

6. The method according to claim 1, wherein in step (d), pullulanase is added in an amount of 30 ASPU/g to 40 ASPU/g dry starch, and α-amylase is added in an amount of 20 ASPU/g to 30 ASPU/g dry starch.

7. The method according to claim 1, wherein in step e, the membrane comprises hollow fiber membranes with molecular weight cutoffs of 5000 Da and 2000 Da.

8. The method according to claim 2, wherein spray drying is performed at an inlet air temperature of 140° C. to 160° C.

9. A method of preparing amylodextrin, which comprises the following steps performed in the following order:
    (a) preparing a 5% to 10% waxy corn starch slurry and stirring evenly,
    (b) exposing the slurry to ultrasonic waves at a frequency of 25 kHz, a power of 600 W, a temperature of 25° C., for 3 second intervals at an interval of 5 seconds, and for a total time of 10 minutes to obtained de-clustered corn starch;
    (c) adding glyceryl monostearate in an amount of 5% mass of the waxy corn starch into the de-clustered corn starch and stirring evenly to create an emulsification,
    (d) exposing the emulsification of (c) to ultrasonic waves at a frequency of 20 kHz, a power of 500 W, at 40° C., for 3 second intervals at an interval of 5 seconds, for 20 minutes total to create a starch-glyceryl monostearate complex solution;
    (e) adjusting a pH value of the starch-glyceryl monostearate complex solution to 6.0 with a phosphate buffer;
    (f) heating the starch-glyceryl monostearate complex solution to 50° C. in a water bath;
    (g) adding α-amylase and pullulanase, at an amount of 30 ASPU/g dry starch for each enzyme to create an enzyme solution;
    (h) incubating the enzyme solution of step (g) in a water bath at 50° C. for 3 to 4 hours;
    (i) incubating the solution of step (h) in boiling water for 5 minutes to inactivate α-amylase and pullulanase;
    (j) centrifuging the inactivated solution of step (i) to obtain a supernatant;
    (j) adding absolute ethanol to the supernatant to dissolve glyceryl monostearate;
    (k) separating the product of step (j) by application to a hollow fiber membrane with molecular weight cutoff of 5000 Da and 2000 Da under conditions that a membrane effective region is 0.4 m², at 40° C. and 15 kPa to obtain separated dextrin; and
    (l) spray drying the dextrin.

10. A method of preparing amylodextrin, which comprises the following steps performed in the following order:
    (a) preparing a 5% to 10% waxy corn starch slurry and stirring evenly,
    (b) exposing the slurry to ultrasonic waves at a frequency of 25 kHz, a power of 600 W, a temperature of 25° C., for 3 second intervals at an interval of 5 seconds, and for a total time of 10 minutes to obtained de-clustered corn starch;

(c) adding palmitic acid in an amount of 3% mass of the waxy corn starch into the de-clustered corn starch and stirring evenly to create an emulsification,
(d) exposing the emulsification of (c) to ultrasonic waves at a frequency of 20 kHz, a power of 500 W, at 40° C., for 3 second intervals at an interval of 5 seconds, for 20 minutes total to create a starch-glyceryl monostearate complex solution;
(e) adjusting a pH value of the starch-palmitic acid complex solution to 6.0 with a phosphate buffer;
(f) heating the starch-palmitic acid complex solution to 50° C. in a water bath;
(g) adding α-amylase and pullulanase at an amount of 20 ASPU/g dry starch and 40 ASPU/g dry starch, respectively, to create an enzyme solution;
(h) incubating the enzyme solution of step (g) in a water bath at 50° C. for 3 to 4 hours;
(i) incubating the solution of step (h) in boiling water for 5 minutes to inactivate α-amylase and pullulanase;
(j) centrifuging the inactivated solution of step (i) to obtain a supernatant;
(j) adding absolute ethanol to the supernatant to dissolve palmitic acid;
(k) separating the product of step (j) by application to a hollow fiber membrane with molecular weight cutoff of 5000 Da and 2000 Da under conditions that a membrane effective region is 0.4 m$^2$, at 40° C. and 15 kPa to obtain separated dextrin; and
(l) spray drying the dextrin.

* * * * *